Figure 3:
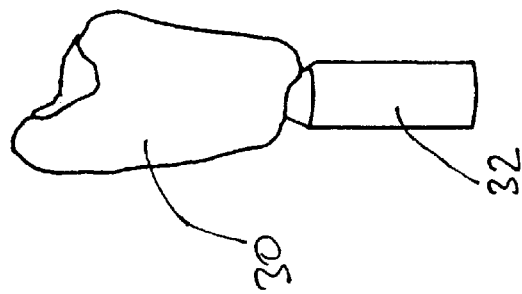

United States Patent [19]
Dörken et al.

[11] Patent Number: 6,099,313
[45] Date of Patent: Aug. 8, 2000

[54] DENTAL IMPLANT, A TEMPLATE FOR INSERTING A DENTAL IMPLANT, AND A PROCESS FOR PRODUCING THEM

[76] Inventors: Wolfgang Dörken, Am Berg 26, D-78247 Hilzingen; Burkhard Gieloff, Alemannenstrasse 19, D-79211 Denzlingen; Gerold Klaus, Tullastrasse 6a, D-79341 Kenzingen; Bernd Rademacher, Rohstrasse 30, D-58093 Hagen, all of Germany

[21] Appl. No.: 09/171,952
[22] PCT Filed: Jun. 27, 1997
[86] PCT No.: PCT/EP97/03383
§ 371 Date: May 13, 1999
§ 102(e) Date: May 13, 1999
[87] PCT Pub. No.: WO98/00072
PCT Pub. Date: Jan. 8, 1998

[30] Foreign Application Priority Data

Jun. 28, 1996 [DE] Germany .............................. 196 25 975

[51] Int. Cl.[7] .............................................. A61C 8/00
[52] U.S. Cl. ...................................... 433/175; 433/173
[58] Field of Search .................................. 433/173, 174, 433/175, 201.1, 223, 75, 76

[56] References Cited

U.S. PATENT DOCUMENTS

| | | |
|---|---|---|
| 4,408,990 | 10/1983 | Misch . |
| 5,133,660 | 7/1992 | Fenick ........................................ 433/76 |
| 5,302,122 | 4/1994 | Milne ......................................... 433/76 |
| 5,320,529 | 6/1994 | Pompa ....................................... 433/76 |
| 5,350,297 | 9/1994 | Cohen ........................................ 433/76 |
| 5,725,376 | 3/1998 | Poirier .................................... 433/75 X |

FOREIGN PATENT DOCUMENTS

| | | |
|---|---|---|
| 82540 | 6/1964 | France . |
| 2468352 | 5/1981 | France . |
| 19513881 | 2/1996 | Germany . |

*Primary Examiner*—Nicholas D. Lucchesi
*Attorney, Agent, or Firm*—Bachman & LaPointe, P.C.

[57] ABSTRACT

The invention concerns a dental implant with a shaped, bone contact section for insertion into the tooth socket of a jaw and a built up section used for fastening a crown or similar material, where the bone contact section has an apical extension section which is made for the insertion into an artificially produced recess in the jaw which deepens the base of the tooth socket.

12 Claims, 2 Drawing Sheets

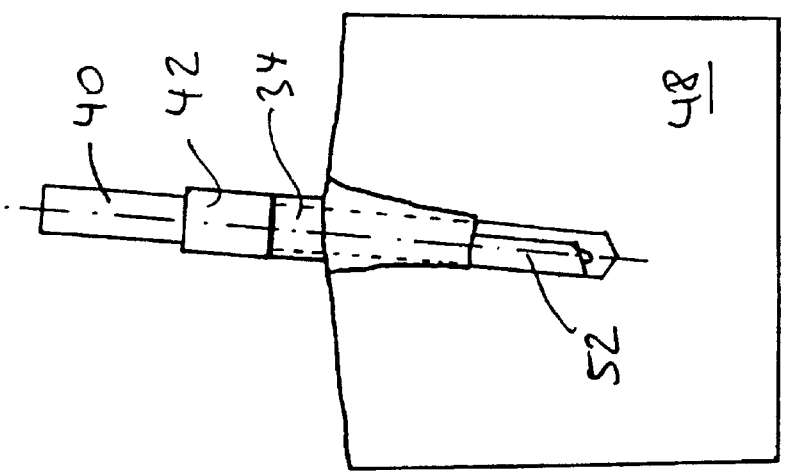
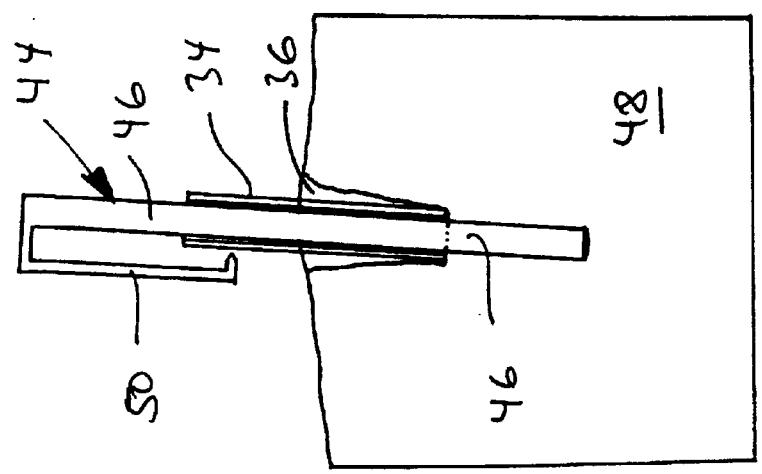
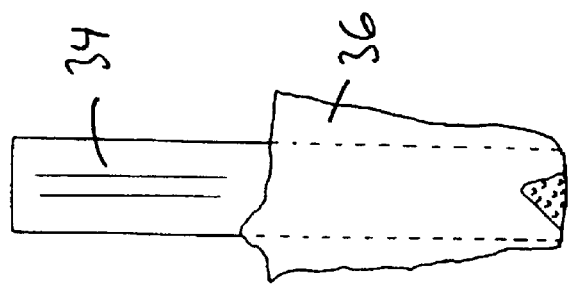

DENTAL IMPLANT, A TEMPLATE FOR INSERTING A DENTAL IMPLANT, AND A PROCESS FOR PRODUCING THEM

The present invention concerns a dental implant of metal material having a bone contact portion for insertion into a tooth cavity of a jaw and a build-up portion for fixing a crown, a process for the production of a dental implant, a template for inserting an implant and a process for the production of such a template.

The implantation of dental implants is a dental method of treatment in which an implant which is a more or less true-to-scale copy of the extracted natural tooth is put back into the alveolus, that is to say the tooth socket. In that respect, the most widely varying shapes of industrially manufactured implants are known in implantology.

The applicants' DE 195 13 881 A1 describes an implant and a process for the production of such an implant, whereby an accurately fitting tooth prosthesis which enjoys long-term stability can be provided in a particularly advantageous manner.

However it is possible to conceive of the medical situation where for example the tooth socket depth is reduced by degeneration of the jaw bone in the region of the socket of the extracted tooth: that can attain such an extent that it is no longer possible to provide for a durable fit, which can carry mechanical loadings, of an implant to be fitted therein, by virtue of the remaining effective tooth socket depth.

A dental implant of metal material having a bone contact portion for insertion into a tooth cavity of a jaw and a build-up portion for fixing a crown is known from FR-A-2 468 352; formed on a root produced from calcined material as a bone contact portion of an implant with small blade portions projecting cross-wise therefrom is a cylindrical axial bar portion with arms projecting therefrom and a stump which delimits it in an upward direction and which tapers away from it. The arms are pins which pass through the axial bar and which are inclined with respect thereto and which cross each other and which project laterally out of its flanks and then engage into the bone. In an upward direction the pins terminate in the region of the stump which serves as a build-up portion. Also shown is a base plate which bridges over the bone for the build-up portion, which is held by the mutually crossing pins—now without implant or artificial root. Those pins of small cross-section can be comparatively long to improve the support thereof in the bone.

Therefore the object of the present invention is so to improve a dental implant of the kind set forth in the classifying portion of the main claim, that secure insertion of implants is possible even for only shallow tooth socket depths: this also applies in regard to situations in which the tooth socket depth is only slight, due to other circumstances. Furthermore, as a system concept, the invention seeks to provide devices and processes for the production of such devices with which reliable secure insertion of such improved implants is possible.

The object of the invention is attained by the dental implant, the production process for a dental implant, the template and the production process for said template as set forth in the present specification.

In accordance with the invention the extension portion is of a diameter which is smaller than the corresponding cross-sectional dimension of the bone contact portion, wherein the latter and/or the extension portion includes on its surface a plurality of honeycombs which are arranged at uniform spacings and which extend—in mutually adjoining relationship—substantially over the entire surface in the manner of a uniform pattern; the extension portion is also of a substantially cylindrical shape.

Advantageously therefore the extension portion according to the invention which is adapted for insertion into an artificially produced opening in the jaw, which deepens the tooth socket at the bottom, extends the apical end of the bone contact portion (which in the present case is intended substantially to mean the region which imitates the extracted tooth root), so that an additional hold and an extended mechanical lever arm in the jaw bone are provided. The dental implant can be provided entirely (that is to say at the bone contact portion and on the extension portion) with the surface structuring which promotes the hold of the implant in the bone; however structuring measures of that kind are also possible selectively, therefore only in the region of the bone contact portion or the extension portion or in partial regions thereof.

In this connection the term "tooth socket" means the socket which has been formed by extraction of the tooth in question, while the opening which is artificially produced in accordance with the claim is formed in the jaw bone by subsequent manipulative measures of a treatment—that is to say for example by drilling or milling.

In a particularly advantageous manner moreover the implant according to the invention is produced by contact-less measurement of the tooth root provided with an extension part (corresponding to the intended extension portion of the implant to be produced), wherein in that way it is possible to optimise the hold and the fitting shape and possible ways of specifically manipulating the measurement data are afforded.

The template according to the invention for inserting a dental implant, by virtue of the particular shape of the tooth root imitation, permits the template to be inserted in a clearly defined and non-rotatable fashion as a prerequisite for reliable drilling; at the same time the drill guide configuration not only prevents unintentional injury to surrounding tissue but at the same time it prevents the drill from being able to penetrate into the jaw deeper than a predetermined maximum drilling depth (corresponding to the extension portion to be inserted).

Advantageous developments of the invention are set forth in the appendant claims.

Thus the extension portion which is of a cylindrical configuration is preferably rounded off at its end—corresponding to the drill head. It can also be particularly advantageous for the extension portion to be slightly angled in order thereby to take account of respective specific orthopaedic conditions in the jaw region and to enhance the stability of the implant in the inserted condition.

It is also advantageous for a cross-sectional diameter of the extension portion to be smaller by a predetermined amount than the corresponding diameter of the artificially produced opening in the jaw.

It is also particularly advantageous for the template to be produced in such a way that the sleeve which serves as a guide in accordance with a further development can at the same time form an abutment for the drill (which has a corresponding shank shoulder). More specifically, in that way the sleeve can be set to an individually suitable dimension at a low level of cost merely by using the measuring gauge which is calibrated with a predetermined length according to the drill used.

Figure 2:
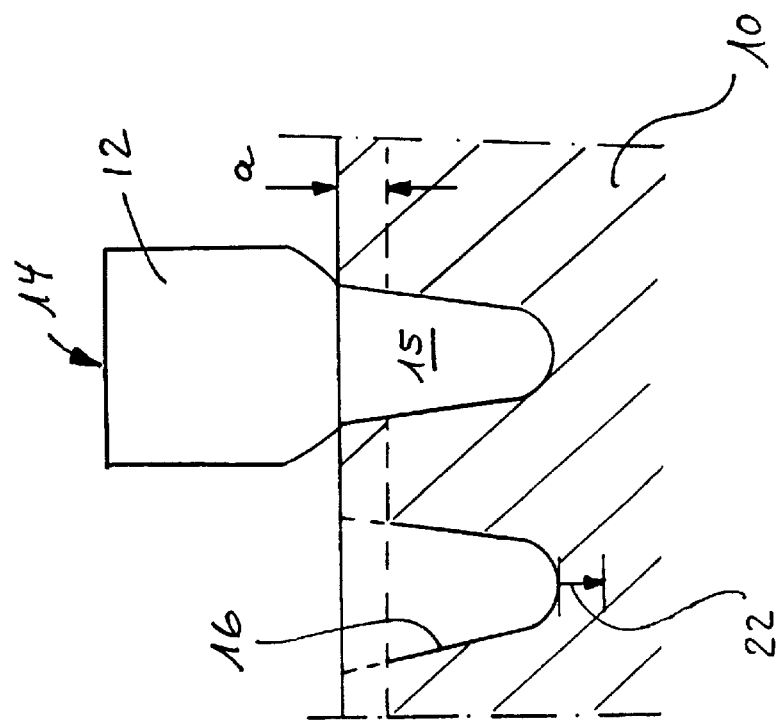
Figure 1:
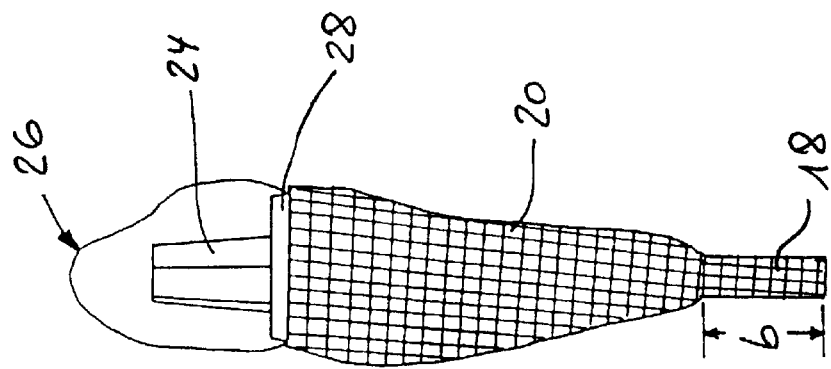

Further advantages, features and details of the invention will be apparent from the following description of preferred embodiments and with reference to the drawing in which:

FIG. 1 is a partly sectional side view of the implant according to the invention in a first embodiment, FIG. 2 is a diagrammatic sectional view through the edge of a human bottom jaw with a sound tooth and a tooth socket after a tooth has been extracted, FIG. 3 is a diagrammatic side view of an extracted tooth root which has apical extension inserted in the region of the root tip, FIG. 4 is a side view of a drilling template for use with the implant according to the invention with a guide sleeve which has not yet been cut to length, FIG. 5 shows the drilling template of FIG. 4, which simulates the tooth root shape, in the condition of being inserted into a molding of the extended root of FIG. 3 with inserted measuring gauge, and FIG. 6 shows the inserted drilling template of FIG. 5 with the guide sleeve cut to length and a drill inserted therein.

Tooth crowns 12 of teeth 14 project from a bottom jaw portion 10 of a human bottom jaw and are held in the jaw portion 10 by a tooth root 15 which is diagrammatically illustrated in FIG. 2.

The tooth which is at the left-hand position in FIG. 2 has been removed by extraction: what remains is an empty alveolus (tooth socket) 16. The gap in the bottom jaw is to be closed by an implant according to the invention, preferably adapted to the extracted tooth root or the tooth socket 16.

As diagrammatically indicated in FIG. 2, there is however frequently a reduction in the length or depth of the tooth cavity by virtue of the fact that the upper edge of the jaw shrinks and drops by a distance a—corresponding to the horizontal broken line in FIG. 2. The consequence of this is that the effective tooth socket length that now remains is no longer sufficient to afford stability and an adequate hold for an implant.

In accordance with the invention therefore the dental implant which is particularly suitable for use in such a situation has an extension portion 18 which is to be fitted to the apical tooth root and which at the bottom extends the implant according to the invention as shown in FIG. 1, in accordance with a first embodiment: more specifically the extension portion extends the effective jaw engagement depth of a bone contact region 20 of the implant according to the invention by an extension depth b of preferably approximately between 10 and 25 mm so that shrinkage at the upper edge of the jaw or the mechanical strength disadvantages thereof can be compensated by suitable—dental—predetermination of b.

As indicated by the arrow 22 in FIG. 2 however additional space for accommodating the extension portion 18 must be provided in the jaw portion 10 (that is to say in the bone) by drilling or like measures.

With the exception of that extension portion 18 the implant shown in FIG. 1 does not differ from known dental implants as are known for example from the applicants' DE 195 13 881 A1 (the disclosure of that specification is deemed to be incorporated in its entirety into the present application); thus the bone contact region 20 is extended at its exit end with respect to the jaw bone by a slightly conically tapering mounting portion 24 which serves to fit on and hold a crown 26. In addition, formed at the location at which the mounting portion 24 is attached to the bone contact region 20 is a groove or concave portion 28 which serves to receive the edge of the crown 26.

In the illustrated embodiment the extension portion 18 is substantially cylindrical and is provided with a surface structure corresponding to that of the bone contact region 20. There, regularly arranged honeycombs are formed over the entire contact surface, forming trough depths of about 0.2 mm (however the invention is not limited to that specific nature of structuring of the bone contact and extension region respectively; any other conventional structuring in respect of those regions or however a substantially smooth external form is alternatively possible).

The shape of the extension portion 18 according to the present invention is also not limited to a cylinder. It would also be possible to conceive of other extensions which improve hold and stability in a mechanically and/or medically suitable manner—for example with a contour which tapers at its end and/or involving a multi-angular, for example polygonal, cross-section.

In addition, depending on the configuration of the respective jaw portion, it may be appropriate for the extension portion 18 not to be formed axially with respect to a longitudinal axis of the implant or the extracted tooth root; on the contrary, the extension portion 18 is angled through a slight angle, through a predetermined angle in dependence for example on anatomical factors (this measure could be necessary for example to prevent perforation of the buccal tooth socket wall).

For securely inserting the implant according to the invention and in particular for guiding the drill for forming the additional bottom depression in the jaw bone, a drilling template is required, which in addition adapts a maximum drilling depth of the drill to the extension dimension b of the extension portion 18. The structure and production of the drilling template are described hereinafter.

As shown in FIG. 3, as a preparatory step the extracted tooth root 30 is drilled in the region of the apical root tip and provided with a screwthread into which an extension shaft portion 32 which can be screwed into the screwthread is inserted and secured therein by gluing. The extension shaft portion 32 is already cut to length to the desired extension dimension and possibly involves the intended slight angle with respect to the longitudinal axis of the root (besides use thereof for production of the drilling template the arrangement shown in FIG. 3 comprising the tooth root 30 and the extension shaft portion 32 is also required as a pattern for production of the implant itself: in known manner the arrangement is coated with laser scanning lacquer and by a scanning-in procedure scanned three-dimensionally and measured. The data obtained in that way can then be used to produce the implant from suitable material—possibly with a preselected oversize or undersize).

In a further process step for template production a molding is now produced by means of a (silicone) molding material from the tooth root 30 extended by the extension portion 32 and the root together with the extension shaft portion is removed from the molding.

Then, fitted in place thereof is a centering shaft portion—not shown in the Figures—over which is pushed a titanium sleeve 34 which is shown in FIG. 4 and which is guided at the end as far as the apical root end of the root molding. The intermediate space between the titanium sleeve 34 and the root molding is then filled up with a filling material, preferably auto-polymer, so that after hardening thereof a tooth root imitation or simulation 36 comprising the hardened filling material, is carried on the titanium sleeve 34. As shown in FIG. 4, for better adhesion of the polymer the titanium sleeve 34 has a structuring provided in the lower peripheral surface region thereof.

The purpose of the titanium sleeve is to guide the drill used for drilling the tooth socket extension in the bottom thereof, in the jaw, and to limit it in terms of its maximum drilling depth. Since, as shown in FIG. 6, for that purpose, use is made of drills 40 whose drilling depth is standardized and limited by an abutment 42 in the form of a shank shoulder, co-operating with the titanium sleeve 34, it is necessary for the titanium sleeve 34 of the drilling template blank which is shown in FIG. 4 to be cut to a suitable length which offers the drill 40 to be used, a limitation in terms of the drilling depth thereof, at a maximum drilling or penetration depth which corresponds to the length b of the extension portion 18.

The measuring gauge 44 shown in FIG. 5 is used for that purpose. The measuring gauge 44 has an elongate, substantially cylindrical shank 46 which can be introduced into the titanium sleeve 34 and guided through the drilling template (shown in FIG. 5 in the condition of being inserted into the molding 48), until the shank 46 bears at the end on the bottom of the extension (formed by the extension shaft portion 32 in FIG. 3). As the measuring gauge 44 with a marking element 50 corresponds to the dimensions of the standardized drill 40 to be used, when the shaft 44 is fully inserted the outside wall of the titanium sleeve 34 can be marked by means of the marking element 50 at the location at which the titanium sleeve 34 is to be cut to length to produce the drilling template.

FIG. 6 then diagrammatically illustrates the sleeve 34 in the suitably shortened condition and with a drill 40 inserted as far as the abutment so that the drill head 52 thereof completely engages into the molding of the extension shaft portion.

FIGS. 5 and 6 also show the slightly angled arrangement of the extension (or the measuring gauge and the drill respectively) with respect to the perpendicular central axis of the tooth root.

Upon insertion by the dentist, the dentist now uses the drilling template which has been produced in accordance with the invention and cut to length and which is fitted into the tooth socket, being cleaned and sterilized immediately before the implantation operation. The drilling operation is then preferably effected in two stages with preliminary milling and main milling as far as the abutment formed by the shank shoulder 42 or the upper edge of the titanium sleeve 34.

Thereupon, it is then possible to insert the above-described implant according to the invention with the extension portion 18 at its end, in which respect the present invention also embraces providing the bone contact region 20 and/or the extension portion 18 with a predetermined oversize or undersize with respect to the tooth socket 16 or the bore at the bottom thereof, in order to influence the hold and the strength of the implant in the jaw bone.

In accordance with a preferred development of the invention the extension portion 18 is reduced in respect of its diameter, in which case a diameter correction of minus 0.2 mm is particularly preferably implemented.

It is also advantageous in accordance with a development for the apical end of the extension portion 18 to be slightly rounded off as the bottom of the bore produced by the drilling head 22 is not right-angled but slightly conical.

What is claimed is:

1. A dental implant which comprises: a bone contact portion which has apically an extension portion thereof and which is adapted for insertion into an artificially produced opening in the jaw, which deepens a tooth socket at a bottom thereof; a build-up portion which serves for fixing a crown or the like attachment; the bone contact portion having a surface and a cross-sectional dimension and the extension portion having a surface and a cross-sectional dimension and the cross-sectional dimension of the extension portion being smaller than the cross-sectional dimension of the bone contact portion; wherein the surface of at least one of the bone contact portion and the extension portion having a plurality of honeycombs which are arranged at uniform spacings and which extend in mutually adjoining relationship substantially over the entire surface thereof in the manner of a uniform pattern; and wherein the extension portion is of a substantially cylindrical shape.

2. An implant as set forth in claim 1, wherein the extension portion has an end thereof and is of a substantially cylindrical shape and is rounded off at the end thereof.

3. An implant as set forth in claim 1, wherein the extension portion has a longitudinal axis which is angled through a predetermined angle with respect to a longitudinal axis of the bone contact portion.

4. An implant as set forth in claim 1, wherein at least one of the surface of the bone contact portion and the surface of the extension portion is roughened.

5. An implant as set forth in claim 1, wherein the bone contact portion simulates the tooth root shape of a tooth to be replaced and is of such a dimension that it forms a press fit when inserted into the tooth pocket.

6. A process for the production of a dental implant which comprises the following steps:

forming an apical extension on an extracted tooth root with an extension portion;

providing a contact-less measurement of the tooth root which i s extended by the extension portion; and forming a simulation of the tooth root which is extended by the extension portion using a biologically compatible, non-resorbable material on the basis of data produced by the measurement step.

7. A process as set forth in claim 6, including the step of:

correcting cross-sectional dimensions of a portion of at least one of the tooth root and the extension portion by a predetermined value prior to the operation of forming the simulation.

8. A process as set forth in claim 7, wherein the operation of forming the simulation is implemented under computer control by one of an erosion process and water-jet cutting.

9. A method of making the dental implant of with claim 1, which comprises the following steps:

forming an apical extension on an extracted tooth root with an extension portion;

providing a contact-less measurement of the tooth root which is extended by the extension portion; and forming a simulation of the tooth root which is extended by the extension portion using a biologically compatible, non-resorbable material on the basis of data produced by the measurement step.

10. A process for producing a drilling template which comprises the following steps:

apically extending an extracted tooth root with an extension portion;

forming a molding of the tooth root which is apically extended by the extension portion;

inserting a sleeve of metal material into the molding so that a first end of the sleeve is in the region of an apical tip of the molded tooth root;

filling a cavity formed between the sleeve and an inside wall surface of the molding with a hardenable material;

hardening said hardenable material; and cutting the sleeve to length at a second end thereof opposite to the first end to produce an abutment for a drill or the like tool, for limiting a maximum drilling depth.

11. A process as set forth in claim 10, wherein the step of cutting the sleeve to length includes the following steps:

inserting a measuring gauge of predetermined length into the sleeve as far as the end of the molding of the extension portion; and marking off a dividing line on the sleeve in the region of the second end by a marking element of the measuring gauge.

12. A process for producing a drilling template for a dental implant in accordance with claim 1, which comprises the following steps:

apically extending an extracted tooth root with an extension portion;

forming a molding of the tooth root which is apically extended by the extension portion;

inserting a sleeve of metal material into the molding so that a first end of the sleeve is in the region of an apical tip of the molded tooth root;

filling a cavity formed between the sleeve and an inside wall surface of the molding with a hardenable material;

hardening said hardenable material; and cutting the sleeve to length at a second end thereof opposite to the first end to produce an abutment for a drill or the like tool, for limiting a maximum drilling depth.

* * * * *